United States Patent
Akerman et al.

(10) Patent No.: US 11,781,123 B2
(45) Date of Patent: *Oct. 10, 2023

(54) PROCESS OF EXTRACTING OIL FROM THIN STILLAGE

(71) Applicant: NOVOZYMES A/S, Bagsvaerd (DK)

(72) Inventors: Michael John Akerman, Wake Forest, NC (US); Nathaniel Edward Kreel, Louisburg, NC (US); Melissa Carrie Hooss, Franklinton, NC (US); Xinyu Shen, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 757 days.

This patent is subject to a terminal disclaimer.

(21) Appl. No.: 16/062,769

(22) PCT Filed: Dec. 16, 2016

(86) PCT No.: PCT/US2016/067154
§ 371 (c)(1),
(2) Date: Jun. 15, 2018

(87) PCT Pub. No.: WO2017/112539
PCT Pub. Date: Jun. 29, 2017

(65) Prior Publication Data
US 2021/0130857 A1    May 6, 2021

Related U.S. Application Data

(60) Provisional application No. 62/430,695, filed on Dec. 6, 2016, provisional application No. 62/324,107, filed on Apr. 18, 2016, provisional application No. 62/271,182, filed on Dec. 22, 2015, provisional application No. 62/271,063, filed on Dec. 22, 2015.

(51) Int. Cl.
| | |
|---|---|
| C12N 9/14 | (2006.01) |
| C12P 19/14 | (2006.01) |
| C12N 9/26 | (2006.01) |
| C12N 9/34 | (2006.01) |
| C12N 9/42 | (2006.01) |
| C12N 9/44 | (2006.01) |
| C12N 9/50 | (2006.01) |
| C12N 9/20 | (2006.01) |
| C12P 7/06 | (2006.01) |
| C12N 9/16 | (2006.01) |
| C12N 9/28 | (2006.01) |
| C12P 7/64 | (2022.01) |

(52) U.S. Cl.
CPC .......... *C12N 9/14* (2013.01); *C12N 9/16* (2013.01); *C12N 9/20* (2013.01); *C12N 9/2414* (2013.01); *C12N 9/2417* (2013.01); *C12N 9/2428* (2013.01); *C12N 9/2437* (2013.01); *C12N 9/2457* (2013.01); *C12N 9/50* (2013.01); *C12P 7/06* (2013.01); *C12P 19/14* (2013.01); *C12Y 301/03008* (2013.01); *C12Y 301/04* (2013.01); *C12Y 301/04011* (2013.01); *C12Y 302/01001* (2013.01); *C12Y 302/01003* (2013.01); *C12Y 302/01004* (2013.01); *C12Y 302/01008* (2013.01); *C12Y 302/01041* (2013.01); *C12Y 304/21062* (2013.01); *C12Y 304/23023* (2013.01); *C12Y 304/24039* (2013.01); *C12P 7/64* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,008,517 B2* | 8/2011 | Cantrell | B01D 3/004 554/8 |
| 8,535,927 B1 | 9/2013 | Jones et al. | |
| 9,279,110 B2* | 3/2016 | Tang | A23D 9/04 |
| 9,528,128 B2* | 12/2016 | Hansen | C12Y 302/01001 |
| 9,816,112 B2* | 11/2017 | Deinhammer | C12Y 302/01003 |
| 10,597,645 B2* | 3/2020 | Jump | C12Y 304/23023 |
| 11,028,378 B2* | 6/2021 | Jump | C12N 9/2417 |
| 2004/0063184 A1 | 4/2004 | | |

FOREIGN PATENT DOCUMENTS

| | | |
|---|---|---|
| EP | 1905821 A1 | 6/2003 |
| WO | 2005079193 A2 | 9/2005 |
| WO | 2011/126897 A2 | 10/2011 |
| WO | 2014/074452 A1 | 5/2014 |
| WO | 2014090161 A1 | 6/2014 |
| WO | 2014/209789 A1 | 12/2014 |
| WO | 2015/116395 A1 | 8/2015 |
| WO | 2015/173246 A1 | 11/2015 |
| WO | 2015173426 A1 | 11/2015 |

OTHER PUBLICATIONS

Majoni et al., 2010, J Am Oil Chem Soc 88(4), 523-532.
Wang et al., 2009, J Agric Food Chem 57(6), 2302-2307.
Devos et al., Proteins: Structure, Function, and Genetics 41, 2000, 98-107, 41.

* cited by examiner

*Primary Examiner* — Hope A Robinson
(74) *Attorney, Agent, or Firm* — David Fazzolare

(57) ABSTRACT

A process of recovering oil, comprising (a) converting a starch-containing material into dextrins with an alpha-amylase; (b) saccharifying the dextrins using a carbohydrate source generating enzyme to form a sugar; (c) fermenting the sugar in a fermentation medium into a fermentation product using a fermenting organism; (d) recovering the fermentation product to form a whole stillage; (e) separating the whole stillage into thin stillage and wet cake; (e') optionally concentrating the thin stillage into syrup; (f) recovering oil from the thin stillage and/or optionally the syrup, wherein a phospholipase is present and/or added during steps (a) to (c). Use of phospholipase for increasing oil recovery yields from thin stillage and/or syrup in a fermentation product production process.

19 Claims, 3 Drawing Sheets

Specification includes a Sequence Listing.

SEQUENCE LISTING

```
<160> NUMBER OF SEQ ID NOS: 5

<210> SEQ ID NO 1
<211> LENGTH: 610
<212> TYPE: PRT
<213> ORGANISM: Penicillium emersonii
<220> FEATURE:
<221> NAME/KEY: SIGNAL
<222> LOCATION: (1)..(16)
<220> FEATURE:
<221> NAME/KEY: mat_peptide
<222> LOCATION: (17)..(610)

<400> SEQUENCE: 1

Met Arg Val Leu Ala Leu Ile Ala Ala Leu Ala Thr Val Ala Thr Ala
    -15                 -10                  -5                  -1

Ser Ala Pro Tyr Asp Lys Arg Asp Leu Ala Gln Glu Ile Trp Asp Asp
  1               5                  10                  15

Ile Lys Asn Ala Val Asp Cys Ala Gly Cys Gln Val Val Leu Thr Ala
                 20                  25                  30

Leu Lys Gly Val Ala Asp Leu Gly Thr Thr Ala Leu Val Asp Val Leu
             35                  40                  45

Thr Glu Val Cys Asn Ile Ser Gly Lys Glu Asp Ser Asp Val Cys Ser
     50                  55                  60

Gly Ile Ile Ser Arg Glu Gly Pro Val Leu Asp Tyr Val Leu Gln His
 65                  70                  75                  80

Leu Asp Ile Gly Ser His Thr Ser Gln Val Ile Cys Ala Ser Ala Phe
                 85                  90                  95

Gly Leu Cys Gln Tyr Pro Glu Val Arg Pro Tyr Asn Leu Thr Phe Pro
                100                 105                 110

Lys Pro Lys Pro Asn Thr Thr Arg Pro Glu Pro Ser Gly Glu Ser Pro
            115                 120                 125

Ile Gln Val Val His Phe Ser Asp Thr His Val Asp Leu Ser Tyr Glu
        130                 135                 140

Thr Gly Ser Asn Tyr Asn Cys Thr Lys Pro Ile Cys Cys Arg Pro Tyr
145                 150                 155                 160

Thr Ala Glu Asp Ala Pro Gly Asn Thr Thr Pro Cys Gly Pro Tyr
                165                 170                 175

Gly Asn Thr Lys Cys Asp Ala Pro Leu Ser Leu Glu Glu Ser Met Phe
            180                 185                 190

Ala Ala Ile Lys Ala Leu Asn Pro Gln Pro Ala Phe Ser Ile Tyr Thr
        195                 200                 205
```

```
Gly Asp Val Val Ala His Asp Ile Trp Leu Val Asp Gln Asn Glu Val
210                 215                 220

Ile Glu Asp Leu Asn Ala Thr Tyr Asp Arg Met Ala Gly Leu Gly Leu
225                 230                 235                 240

Val Tyr Ala Ala Ile Gly Asn His Asp Thr Ala Pro Val Asn Asp Leu
                245                 250                 255

Pro Thr Ser Asn Ile Pro Ser Glu Tyr Ser Ala Asn Trp Thr Tyr Glu
            260                 265                 270

Ala Leu Ser Tyr Asp Phe Thr Met Leu Thr Gln Ser Ala Ser Ala Gln
        275                 280                 285

Thr Ala Ala Asn Tyr Gly Ser Tyr Ser Ala Ile Tyr Pro Gly Ser Tyr
290                 295                 300

Gly Thr Asp Leu Arg Val Ile Ser Tyr Asn Ser Ile Phe Tyr Tyr Val
305                 310                 315                 320

Asp Asn Phe Trp Ala Tyr Gln Asp Pro Met Glu Phe Asp Pro Asp Gly
                325                 330                 335

Gln Leu Ala Trp Leu Ile Asn Glu Leu Gln Glu Ala Glu Thr Ala Gly
            340                 345                 350

Gln Arg Val Trp Ile Ile Ala His Val Pro Thr Gly Thr Ser Asp His
        355                 360                 365

Phe His Asp Tyr Ser His Tyr Phe Asp Gln Ile Val Gln Arg Tyr Glu
370                 375                 380

Ala Thr Ile Ala Ala Leu Phe Tyr Gly His Thr His Ile Asp Gln Phe
385                 390                 395                 400

Gln Ile Ser Tyr Ser Asn Tyr Ser Asn Arg Ala Phe Asp Thr Ala Thr
                405                 410                 415

Ala Ile Gly Tyr Ile Met Pro Ser Leu Thr Pro Thr Ser Gly Pro Pro
            420                 425                 430

Thr Phe Arg Val Tyr Asp Val Asp Pro Lys Thr Phe Ala Val Leu Asp
        435                 440                 445

Phe Thr Asn Tyr Ile Ala Asn Ile Ser Asp Pro Ala Phe Gln Ser Gly
450                 455                 460

Pro Ser Trp Gln Lys Tyr Tyr Ser Ala Lys Glu Thr Tyr Gly Ser Leu
465                 470                 475                 480

Leu Ser Pro Pro Val Thr Asp Pro Thr Ala Glu Leu Thr Pro Ala Phe
                485                 490                 495

Trp His Asn Val Thr Val Ala Phe Glu Gln Asp Asn Ala Thr Phe Gln
            500                 505                 510

Glu Tyr Trp Ala Arg Gln Thr Arg Gly Tyr Asp Val Ser Ser Cys Thr
        515                 520                 525

Gly Ser Cys Ile Thr Gln Ala Ile Cys Gly Leu Arg Ala Gly Asp Ala
530                 535                 540

Gln Tyr Asn Cys Val Thr Pro Thr Pro Gly Phe Asn Phe Ala Lys Arg
545                 550                 555                 560

Asp Thr Ser Asn Pro Lys Gln Ala Leu Ser His Val Glu Lys Cys Glu
                565                 570                 575

Gly Ser Gly Leu Leu Gly Leu Leu Arg Arg Met Val Ala Asp Ser Lys
            580                 585                 590

Ser Ser

<210> SEQ ID NO 2
<211> LENGTH: 278
<212> TYPE: PRT
```

```
<213> ORGANISM: Bacillus thuringensis
<220> FEATURE:
<221> NAME/KEY: SIGNAL
<222> LOCATION: (1)..(33)
<220> FEATURE:
<221> NAME/KEY: mat_peptide
<222> LOCATION: (34)..(278)

<400> SEQUENCE: 2

Met Lys His His Arg Phe Arg Thr Asn Leu Leu Ser Ala Leu Ser Val
            -30                 -25                 -20

Ser Ser Ile Val Ile Thr Ser Ile Ile Gly Ser Thr Gln Thr Thr Tyr
        -15                 -10                 -5

Ala Trp Ser Ala Asp Ala Pro His Asp Pro Asn Gln Ser Thr His Leu
-1  1               5                   10                  15

Phe Ile Val Asn Gly Ala Val Asn Leu Val Ala Asn Asn Thr Asp Pro
                20                  25                  30

Gln Ile Asn Lys Pro Thr Ala Leu Leu Gln Gln Trp Arg Ser Gln Trp
            35                  40                  45

Glu Gln Gly Leu Tyr Asp Ala Asp His Leu Asn Pro Tyr Tyr Asp Ser
        50                  55                  60

Gly Thr Phe Met Ser His Phe Tyr Asp Pro Asp Thr Gln Thr Asn Tyr
    65                  70                  75

Ala Gly Leu Ser Tyr Pro Thr Ala Arg Gln Thr Gly Ala Lys Tyr Phe
80                  85                  90                  95

Thr Ile Ala Ser Asn Asp Tyr Gln Ala Gly Asp Met Ser Asp Ala Phe
                100                 105                 110

Tyr Asn Leu Gly Leu Ser Leu His Tyr Phe Thr Asp Val Thr Met Pro
            115                 120                 125

Leu His Ala Gly Asn Ile Ser Asn Leu Asp His Glu Ala Pro Gly Tyr
        130                 135                 140

His Ala Lys Leu Glu Ala Tyr Ala Glu Ser Ile Gln Asn Gln Val Thr
    145                 150                 155

Pro Pro Thr Ala Gly Leu Tyr Asn Trp Val Ser Pro Asn Asp Pro Glu
160                 165                 170                 175

Leu Trp Ile His Gln Ala Ala Val Gln Ala Lys Ser Val Leu Pro Gln
                180                 185                 190

Val Trp Asn Ser Asp Ile Thr Ser Trp Phe Trp Glu Ala Ala Phe Ser
            195                 200                 205

Asn Tyr Tyr Ser Gln Gln Trp His Asn Ala Val Thr Thr Pro Val Leu
        210                 215                 220

Asn Gln Leu Ser Gln Ala Glu Ala Glu Thr Ala Gly Tyr Ile Asp Leu
    225                 230                 235

Phe Phe Arg Val Asn Gly
240                 245

<210> SEQ ID NO 3
<211> LENGTH: 640
<212> TYPE: PRT
<213> ORGANISM: Kionochaeata sp
<220> FEATURE:
<221> NAME/KEY: SIGNAL
<222> LOCATION: (1)..(18)
<220> FEATURE:
<221> NAME/KEY: mat_peptide
<222> LOCATION: (19)..(640)

<400> SEQUENCE: 3

Met Arg Thr Ser Ser Ile Leu Ser Leu Ala Leu Gly Ala Ser Val Ala
```

-continued

```
              -15             -10              -5
Gln Ala Ala Val Ser Pro Ala Asp Val Leu Ala Val Glu Lys Arg
 -1  1               5                  10

Val Asp Pro Ala Ser Gly Leu Glu Ala Arg Ser Ile Trp Asp Thr Ile
 15              20              25              30

Trp Asp Ile Lys Ser Ala Ala Asp Cys Thr Ala Cys Glu Ala Val
             35              40              45

Leu Thr Leu Leu Lys Gly Val Ala Ala Phe Gly Asp Ser Phe Phe Val
             50              55              60

Glu Val Leu Thr Glu Ile Cys Asp Leu Ser Gly Ala Glu Asp Asp
             65              70              75

Val Cys Ser Gly Val Leu Ser Leu Glu Gly Pro Ile Leu Ala Asn Asp
 80              85              90

Ile Arg Lys Met Ser Ile Gly Ser Lys Thr Ser Glu Leu Phe Cys Ile
 95             100             105             110

Thr Phe Leu Gly Leu Cys Ser Tyr Pro Asp Val Asp Ala Tyr Lys Val
            115             120             125

Pro Phe Pro Thr Ala Ser Ser Ala Ala Thr Arg Pro Val Ser Ser Gly
            130             135             140

Lys Asp Pro Leu Tyr Val Val His Phe Ser Asp Ile His Ile Asp Pro
            145             150             155

Phe Tyr Val Ala Gly Ser Ala Ser Asn Cys Thr Lys Pro Ile Cys Cys
160             165             170

Arg Asp Tyr Thr Ser Ala Ser Ser Pro Gly Asn Asn Asp Ser Pro Ala
175             180             185             190

Gly Pro Tyr Gly Asp His Asn Cys Asp Val Pro Tyr Ser Leu Glu Asp
            195             200             205

Ser Met Tyr Ala Ala Ile Lys Glu Leu Val Pro Asn Ala Ala Phe Gly
            210             215             220

Ile Phe Thr Gly Asp Ile Val Asp His Ala Val Trp Asn Thr Ser Glu
            225             230             235

Ser Gln Asn Ile Ile Asp Met Asn Asp Ala Tyr Ser Arg Met Lys Ser
240             245             250

Ser Gly Met Leu Pro Ala Ile Phe Ala Thr Ala Gly Asn His Glu Ala
255             260             265             270

Ser Pro Val Asn Ala Phe Pro Pro Ala Val Gly Lys Glu Ser Gln
            275             280             285

Trp Val Tyr Asp Thr Leu Ala Ser Asp Trp Ser Gln Trp Ile Gly Ala
            290             295             300

Ser Ala Ala Ser Ser Val Glu Ser Gln Gly Ala Tyr Ser Val Leu Tyr
            305             310             315

Gly Ser Thr Lys Leu Arg Ile Ile Ser Leu Asn Thr Asn Met Tyr Tyr
            320             325             330

Ile Glu Asn Phe Tyr Leu Tyr Glu Pro Thr Met Glu Thr Asp Pro Ala
335             340             345             350

Gly Gln Phe Ala Trp Leu Val Ser Glu Leu Ser Ala Ala Glu Ala Ala
            355             360             365

Gly Glu Arg Val Trp Ile Gly His Met Pro Met Gly Leu Ser Asp
            370             375             380

Ala Phe His Asn Pro Ser Asn Tyr Phe Asp Gln Ile Val Asn Arg Tyr
            385             390             395

Gln Ala Thr Ile Ala Ala Leu Phe Phe Gly His Thr His Glu Asp His
            400             405             410
```

-continued

```
Phe Gln Ile Ser Tyr Ser Asp Tyr Gly Ala Gln Thr Ala Ala Asn Ala
415                 420                 425                 430

Arg Ala Ile Ser Tyr Ile Met Pro Ser Leu Thr Pro Thr Ser Gly His
                435                 440                 445

Pro Thr Phe Arg Val Tyr Ala Val Asp Pro Glu Thr Phe Gly Val Leu
            450                 455                 460

Asp Ala Thr Thr Tyr Tyr Ala Asp Met Gly Leu Ala Ser Tyr Gln Thr
        465                 470                 475

Ala Gly Pro Thr Trp Lys Pro Tyr Tyr Ser Ala Arg Asp Ala Tyr Gly
    480                 485                 490

Gly Leu Val Asp Pro Pro Leu Pro Ala Gly Ala Glu Leu Thr Pro Ala
495                 500                 505                 510

Phe Trp His Asn Val Thr Ala Ala Leu Ala Ala Asn Gln Thr Ser Phe
                515                 520                 525

Asp Ala Tyr Tyr Ala Arg Lys Thr Arg Gly Trp Asp Val Ala Pro Cys
            530                 535                 540

Thr Gly Ala Cys Ala Thr Ala Glu Ile Cys Ala Leu Arg Ala Ala Arg
        545                 550                 555

Ala Gln Asn Asn Cys Val Val Pro Thr Pro Gly Val His Phe Ser Lys
    560                 565                 570

Arg Ala Thr Asp Glu Ala Glu Gly Ala His His Arg Asp Glu Cys Gly
575                 580                 585                 590

Ile Ser Val Ala Arg Asn Ser Leu Ser Leu Val Ala Arg Arg Glu
                595                 600                 605

Ala Leu Glu His Leu Glu Ser Arg Leu Val Glu Arg Arg Ala Val
            610                 615                 620

<210> SEQ ID NO 4
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 4

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
```

```
            145                 150                 155                 160
        Phe Asp Gly Val Asp Trp Asp Glu Ser Arg Lys Leu Ser Arg Ile Tyr
                        165                 170                 175
        Lys Phe Arg Gly Ile Gly Lys Ala Trp Asp Trp Glu Val Asp Thr Glu
                        180                 185                 190
        Asn Gly Asn Tyr Asp Tyr Leu Met Tyr Ala Asp Leu Asp Met Asp His
                        195                 200                 205
        Pro Glu Val Val Thr Glu Leu Lys Asn Trp Gly Lys Trp Tyr Val Asn
        210                 215                 220
        Thr Thr Asn Ile Asp Gly Phe Arg Leu Asp Ala Val Lys His Ile Lys
        225                 230                 235                 240
        Phe Ser Phe Phe Pro Asp Trp Leu Ser Tyr Val Arg Ser Gln Thr Gly
                        245                 250                 255
        Lys Pro Leu Phe Thr Val Gly Glu Tyr Trp Ser Tyr Asp Ile Asn Lys
                        260                 265                 270
        Leu His Asn Tyr Ile Thr Lys Thr Asn Gly Thr Met Ser Leu Phe Asp
                        275                 280                 285
        Ala Pro Leu His Asn Lys Phe Tyr Thr Ala Ser Lys Ser Gly Gly Ala
                        290                 295                 300
        Phe Asp Met Arg Thr Leu Met Thr Asn Thr Leu Met Lys Asp Gln Pro
        305                 310                 315                 320
        Thr Leu Ala Val Thr Phe Val Asp Asn His Asp Thr Glu Pro Gly Gln
                        325                 330                 335
        Ala Leu Gln Ser Trp Val Asp Pro Trp Phe Lys Pro Leu Ala Tyr Ala
                        340                 345                 350
        Phe Ile Leu Thr Arg Gln Glu Gly Tyr Pro Cys Val Phe Tyr Gly Asp
                        355                 360                 365
        Tyr Tyr Gly Ile Pro Gln Tyr Asn Ile Pro Ser Leu Lys Ser Lys Ile
                        370                 375                 380
        Asp Pro Leu Leu Ile Ala Arg Arg Asp Tyr Ala Tyr Gly Thr Gln His
        385                 390                 395                 400
        Asp Tyr Leu Asp His Ser Asp Ile Ile Gly Trp Thr Arg Glu Gly Val
                        405                 410                 415
        Thr Glu Lys Pro Gly Ser Gly Leu Ala Ala Leu Ile Thr Asp Gly Pro
                        420                 425                 430
        Gly Gly Ser Lys Trp Met Tyr Val Gly Lys Gln His Ala Gly Lys Val
                        435                 440                 445
        Phe Tyr Asp Leu Thr Gly Asn Arg Ser Asp Thr Val Thr Ile Asn Ser
        450                 455                 460
        Asp Gly Trp Gly Glu Phe Lys Val Asn Gly Gly Ser Val Ser Val Trp
        465                 470                 475                 480
        Val Pro Arg Lys Thr Thr Val Ser Thr Ile Ala Arg Pro Ile Thr Thr
                        485                 490                 495
        Arg Pro Trp Thr Gly Glu Phe Val Arg Trp Thr Glu Pro Arg Leu Val
                        500                 505                 510
        Ala Trp Pro
        515

<210> SEQ ID NO 5
<211> LENGTH: 583
<212> TYPE: PRT
<213> ORGANISM: Artificial Sequence
<220> FEATURE:
<223> OTHER INFORMATION: Hybrid protein sequence
```

<400> SEQUENCE: 5

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415
```

```
Val Ser Ser Asp Gly Thr Val Thr Phe Asn Leu Lys Asp Gly Leu Pro
            420                 425                 430
Ala Ile Phe Thr Ser Ala Thr Gly Gly Thr Thr Thr Thr Ala Thr Pro
            435                 440                 445
Thr Gly Ser Gly Ser Val Thr Ser Thr Ser Lys Thr Thr Ala Thr Ala
            450                 455                 460
Ser Lys Thr Ser Thr Ser Thr Ser Ser Thr Ser Cys Thr Thr Pro Thr
465                 470                 475                 480
Ala Val Ala Val Thr Phe Asp Leu Thr Ala Thr Thr Thr Tyr Gly Glu
                485                 490                 495
Asn Ile Tyr Leu Val Gly Ser Ile Ser Gln Leu Gly Asp Trp Glu Thr
            500                 505                 510
Ser Asp Gly Ile Ala Leu Ser Ala Asp Lys Tyr Thr Ser Ser Asp Pro
            515                 520                 525
Leu Trp Tyr Val Thr Val Thr Leu Pro Ala Gly Glu Ser Phe Glu Tyr
            530                 535                 540
Lys Phe Ile Arg Ile Glu Ser Asp Asp Ser Val Glu Trp Glu Ser Asp
545                 550                 555                 560
Pro Asn Arg Glu Tyr Thr Val Pro Gln Ala Cys Gly Thr Ser Thr Ala
                565                 570                 575
Thr Val Thr Asp Thr Trp Arg
                580
```

PROCESS OF EXTRACTING OIL FROM THIN STILLAGE

CROSS-REFERENCE TO RELATED APPLICATIONS

This application is a 35 U.S.C. 371 national application of international application no. PCT/US2016/067154 filed Dec. 16, 2016, which claims priority or the benefit under 35 U.S.C. 119 of U.S. application Nos. 62/271,182, 62/271, 063, 62/324,107 and 62/430,695, filed Dec. 22, 2015, Dec. 22, 2015, Apr. 18, 2016 and Dec. 6, 2016, respectively, the contents of which are fully incorporated herein by reference.

FIELD OF THE INVENTION

The present invention relates to processes of extracting/recovering oil from thin stillage and/or syrup at the backend of a fermentation product production process based on starch-containing material.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35% and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles). An increasing number of ethanol plants extract oil from the thin stillage and/or syrup/evaporated centrate as a by-product for use in biodiesel production or other biorenewable products.

Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation product to form whole stillage; separating the whole stillage into thin stillage and wet cake; and recovering oil from the thin stillage. The fermentation medium may further comprise a protease.

WO 2014/209789 (Novozymes) discloses processes of recovering oil after liquefaction and/or from thin stillage and/or syrup/evaporated centrate from a fermentation product production process by adding a thermostable protease to the whole stillage, thin stillage and/or syrup It is an object of the present invention to provide processes for increasing the amount of recoverable oil from fermentation product production processes.

SUMMARY OF THE INVENTION

The object of the present invention is to provide improved processes of extracting or recovering oil at the backend of a fermentation product production process, such as especially an ethanol production process.

Therefore, in the first aspect the invention relates to processes of recovering oil, comprising:

(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (a) to (c).

In a preferred embodiment the phospholipase is a phospholipase C.

In an embodiment the phospholipase, in particular phospholipase C, is combined with a protease.

In an embodiment the phospholipase, in particular phospholipase C, is present and/or added during step (b) and/or step (c). Step (a) may be carried out above the initial gelatinization temperature, such as between 70-100° C., preferably between 80-90° C., such as around 85° C.

Steps (b) and (c) may be carried out simultaneously or sequentially. In embodiments steps (a), (b) and (c) are carried our simultaneously or sequentially. When steps (a), (b) and (c), or steps (b) and (c), are carried out simultaneously, the temperature is below the initial gelatinization temperature, such as between 20-60° C. preferably between 25-40° C., such as around 32° C.

The oil may according to the invention be recovered from the thin stillage and/or syrup/evaporated centrate, e.g., by extraction, such as hexane extraction, or by using another oil recovery technology well-known in the art.

In an embodiment steps (a)-(c) are carried out at a temperature below the initial gelatinization temperature. In another embodiment steps (b) and/or (c) are carried out at a temperature below the initial gelatinization temperature.

In preferred embodiments the phospholipase is selected from the group derived from *Kionochaeata* sp. (e.g., SEQ ID NO: 3), *Penicillium emersonii* (e.g., SEQ ID NO: 1) and *Bacillus thuringiensis* (e.g., SEQ ID NO: 2). Phospholipase C from *Penicillium emersonii* (SEQ ID NO: 1 herein) is preferred.

In another aspect the invention relates to the use of a phospholipase, in particular phospholipase C, for oil recovery from thin stillage and/or syrup at the backend of a fermentation product production process based on starch-containing material.

In an embodiment the phospholipase is combined with a surfactant.

DETAILED DESCRIPTION OF THE INVENTION

Figure 1:
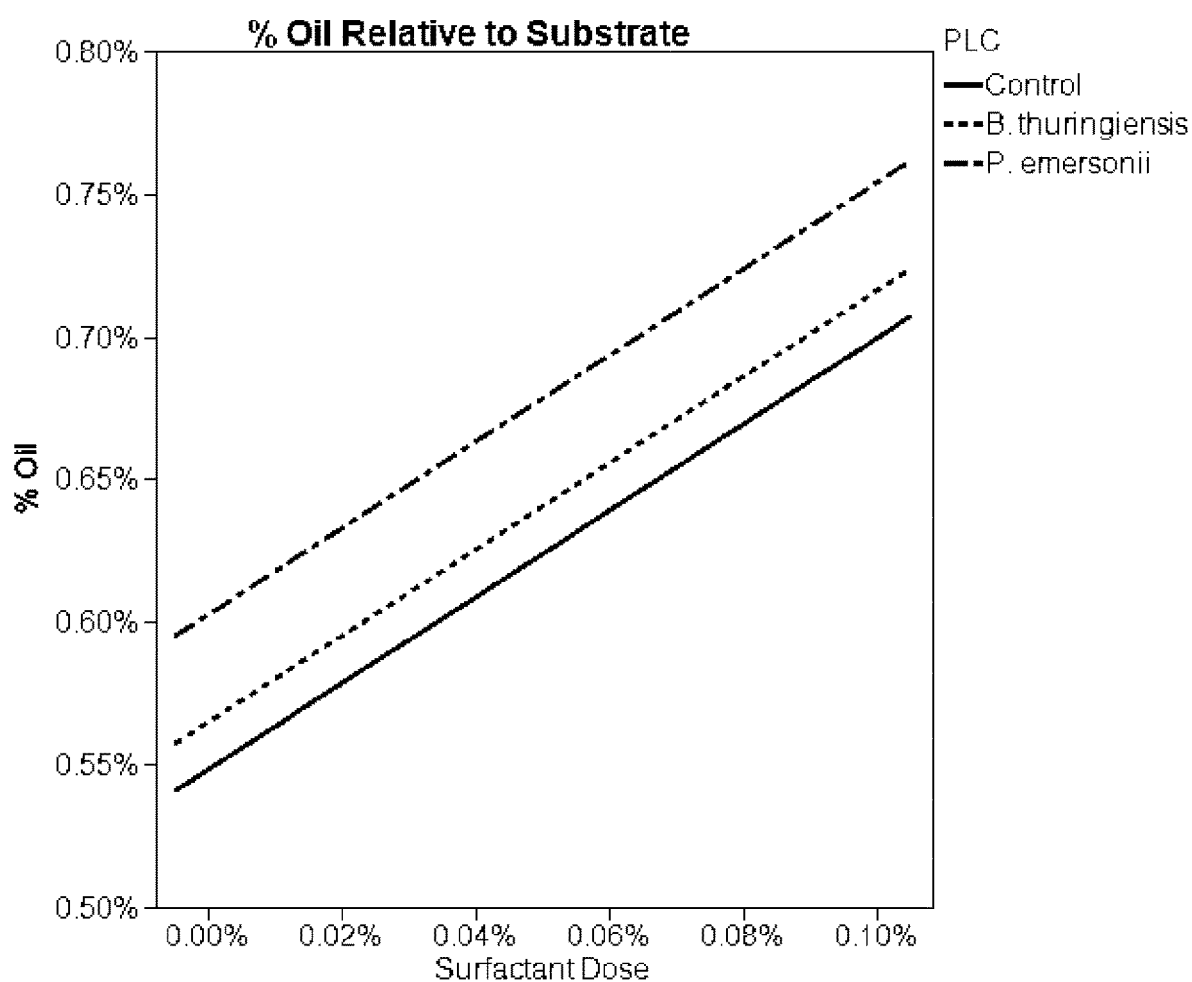
FIG. 1 shows the % oil relative to substrate dose.

The object of the present invention is to provide processes of extracting or recovering oil at the backend of fermentation product production processes, such as especially the thin stillage from an ethanol production processes.

The invention relates to using a phospholipase, in particular a phospholipase C, for recovery/extraction of oil at the back end of a fermentation product production process, in particular from thin stillage from an ethanol manufacturing process. The inventors have surprisingly found that when using a phospholipase alone, in particular phospholipase C, or in combination with a surfactant, in particular non-ionic surfactant(s), the oil recovery yield is increased. Alternatively, the amount of surfactant(s) can be reduced.

Therefore, in the first aspect the invention relates to processes of recovering oil, comprising:

(a) converting a starch-containing material into dextrins with an alpha-amylase;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (a) to (c) (i.e., one or more of steps (a), (b) and (c)).

In an embodiment the phospholipase is present and/or added during steps (b) and/or (c).

In a preferred embodiment the phospholipase is a phospholipase C.

In an embodiment the phospholipase, in particular phospholipase C, is combined with a protease.

In an embodiment one or more surfactants, preferably non-ionic surfactants, are present and/or added. In a preferred embodiment the surfactant(s) are added and/or present in step (b) and/or step (c). The surfactant(s) is(are) preferably non-ionic surfactants, in particular selected from the group of polyethylene glycol sorbitan monooleate (e.g., TWEEN™ 80) and sorbitane monooleate (e.g., SPAN™ 80), or a mixture thereof, such as a 50:50(%) mixture thereof.

In an embodiment a protease is added during steps (a) to (c), preferably steps (b) and/or (c).

Examples of phospholipases, present and/or added in steps (a) to (c), preferably steps (b) and/or (c), includes those having the amino acid sequences of SEQ ID NO: 3 herein (e.g., from a strain of *Kionochaeta*); SEQ ID NO: 1 herein (e.g., from a strain of *Penicillium*); and SEQ ID NO: 2 herein (e.g., from a strain of *Bacillus*). Preferred is the phospholipase having the amino acid sequence of SEQ ID NO: 1 herein, e.g., derived from a strain of *Penicillium emersonii*.

In a preferred embodiment the phospholipase is derived, e.g., from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

In an additional embodiment the phospholipase may be derived from, e.g., *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

In an embodiment the phospholipase may be derived from, e.g., *Kionochaeta*, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

In an embodiment the process of recovering oil of the invention, comprises:

(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (b) and/or (c), When step (a) is carried out as a liquefaction step at high temperatures, i.e., above the initial gelatinization temperature, such as at temperatures between 70-100° C., preferably between 80-90° C., such as around 85° C., the alpha-amylase is preferably a bacterial alpha-amylase.

In a preferred embodiment the alpha-amylase used in step (a), when the temperature in step (a) is above the initial gelatinization temperature, is a bacterial alpha-amylase.

Especially preferred are bacterial alpha-amylases derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 4 herein, in particular a *Bacillus stearothermophilus* alpha-amylase truncated, preferably to be from 485-495 amino acids long, such as around 491 amino acids long.

In a preferred embodiment the bacterial alpha-amylase is selected from the group of *Bacillus stearothermophilus* alpha-amylase variants comprising a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181+G182 compared to the amino acid sequence of *Bacillus stearothermophilus* alpha-amylase set forth as SEQ ID NO: 3 disclosed in WO 99/19467 or SEQ ID NO:

4 herein or the deletion of amino acids R179 and G180 using SEQ ID NO: 3 in WO 99/19467 or SEQ ID NO: 4 herein for numbering.

In an embodiment the bacterial alpha-amylase is selected from the group of *Bacillus stearothermophilus* alpha-amylase variants with the one of the following set of mutations:

I181*+G182*;
I181*+G182*+N193F;
preferably
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A  Q89R+E129V+K177L+ R179E+Q254S+M284V; and
I181*G182*+N193F+E129V+K177D+R179E+K220P+ N224L+S242Q+Q254S (using SEQ ID NO: 4 for numbering).

The parent *Bacillus stearothermophilus* alpha-amylase may be the one shown in SEQ ID NO: 4 herein or may be one having sequence identity thereto of at least 60%, at least 70%, at least 80%, at least 90%, at least 95%, at least 96%, at least 97%, at least 98%, at least 99%.

The *Bacillus stearothermophilus* alpha-amylase variant may be a variant of the one shown in SEQ ID NO: 4 or may be one having sequence identity thereto of at least 60%, at least 70%, at least 80%, at least 90%, at least 95%, at least 96%, at least 97%, at least 98%, at least 99%, but less than 100%.

In an embodiment the *Bacillus stearothermophilus* alpha-amylase variant has from 1-12 mutations, such as 1, 2, 3, 4, 5, 6, 7, 8, 9, 10, 11, or 12 mutations, compared to the parent alpha-amylase, especially the parent alpha-amylase shown in SEQ ID NO: 4.

In an embodiment the pH in step (a) is from 4-7, preferably 4.5-6.

Step (a) is followed by saccharification of dextrins in step (b). However, a process of the invention may further comprise a pre-saccharification step, i.e., after step (a), but before saccharification step (b), carried out for 40-90 minutes at a temperature between 30-65° C.

When step (a) is carried out at a temperature above the initial gelatinization temperature a jet-cooking step may be carried out before in step (a), Jet-cooking may be carried out at a temperature between 95-140° C. for about 1-15 minutes, preferably for about 3-10 minutes, especially around about 5 minutes, In a preferred embodiment a process of the invention further comprises, before step (a), the steps of:
i) reducing the particle size of the starch-containing material, preferably by dry milling;
ii) forming a slurry comprising the starch-containing material and water.

In an embodiment the process of recovering oil of the invention comprises
(a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a phospholipase is present and/or added during steps (a) to (c).

In a preferred embodiment the saccharification step (b) and fermentation step (c) are carried out simultaneously, preferably at a temperature below the initial gelatinization temperature, or sequentially.

In an embodiment steps (a), (b), and (c) are carried out simultaneously. This is typically done at a temperature below the initial gelatinization temperature, i.e. raw starch hydrolysis process (RSH). However, steps (a), (b), and (c) may also be carried out sequentially at temperatures below the initial gelatinization temperature, such as between 20-60° C., preferably between 25-40° C., such as around 32° C.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C, Starch/Starke, Vol. 44 (12) pp. 461-466 (1992).

According to the invention saccharification step (b) may be carried out at a temperature from 20-75° C., preferably from 40-70° C., such as around 60'C, and at a pH between 4 and 5.

In a preferred embodiment fermentation step (c) or simultaneous saccharification and fermentation (SSF) (i.e., combined steps (b) and (c)) are carried out at a temperature between 20-60° C., preferably between 25-40° C., such as around 32° C. In an embodiment fermentation step (c) or simultaneous saccharification and fermentation (SSF) (i.e., combined steps (b) and (c)) are ongoing for 6 to 120 hours, in particular 24 to 96 hours. In an embodiment the starch-containing material converting step (a), saccharification step (b) and fermentation step (c) are carried out simultaneously or sequentially.

In an embodiment the starch-containing material converting step (a) is carried out at a temperature below the initial gelatinization temperature, preferably from 20-60° C., preferably between 25-40° C., such as around 28-36° C., such as around 32° C. In an embodiment the starch-containing material is converted to dextrins and the dextrins are saccharified to a sugar by treating the starch-containing material with an alpha-amylase and carbohydrate-source generating enzyme, in particular a glucoamylase, below the initial gelatinization temperature of the starch-containing material. In an embodiment the conversion of the starch-containing material to dextrins, the saccharification of the dextrins to sugars, and the fermentation of the sugars are carried out in a single step (i.e., raw starch hydrolysis step).

When the process of the invention is carried out as a raw starch hydrolysis process (i.e., single step process or no-cook process) the glucoamylase may preferably be derived from a strain of *Trametes*, such as a strain of *Trametes cingulata*, or a strain of *Athelia*, such as a strain of *Athelia rolfsii*. Preferred alpha-amylases used in a raw starch hydrolysis process include alpha-amylases derived from a strain *Rhizomucor*, such as a strain of *Rhizomucor pusillus*, such as a *Rhizomucor pusilius* alpha-amylase with a starch-binding domain (SBD), such as a *Rhizomucor pusillus* alpha-amylase with *Aspergillus niger* glucoamylase linker and SBD. Generally the starch-containing material in raw starch hydrolysis processes (i.e., no-cook processes) are granular starch. Said granular starch may be reduced the particle size, preferably by milling, to from 0.05 to 3.0 mm, preferably 0.1-0.5 mm.

Also the sugar level, such as glucose level, may be kept below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. The pH may be from 4-7, preferably 4.5-6.0, when conversion of the starch-containing material to dextrins, the saccharification of the dextrins to a sugar, and the fermentation of the sugar are carried out in a single step. If the process of the invention is carried out as a conventional process (i.e., step (a) is carried out as a liquefaction step at a temperature above the gelatinization temperature) the carbohydrate-source generating enzyme used in step (b) is preferably a glucoamylase derived from *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*, or a strain of *Pycnoporus*, or a strain of *Gloephyllum*.

Examples of other suitable glucoamylase can be found below in the "Glucoamylases" section below.

Generally the starch-containing material in step (a), including granular starch, contains 20-55 wt.-% dry solids, preferably 25-40 wt-% dry solids, more preferably 30-35% dry solids.

Separation (i.e. dewatering) in step (e) may be carried out by centrifugation, preferably a decanter centrifuge, filtration, preferably using a filter press, a screw press, a plate-and-frame press, a gravity thickener or decker or any other separation technology known in the art.

The (desired) fermentation product may in an embodiment be selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. In a preferred embodiment the (desired) fermentation product is ethanol. According to the invention the desired fermentation product may be recovered by distillation. According to the invention oil may be recovered from the thin stillage and/or syrup/evaporated centrate, e.g., by extraction, such as hexane extraction.

Separating (Dewaterinq) Whole Stillage into Thin Stillage and Wet Cake in Step (e) Separating whole stillage into thin stillage and wet cake in step (e), in order to remove a significant portion of the liquid/water, may be done using any suitable separation technique, including centrifugation, pressing and filtration. In a preferred embodiment the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment the separation is carried out using other conventional separation equipment such as a plate/frame filter presses, belt filter presses, screw presses, gravity thickeners and deckers, or similar equipment.

Drying of Wet Cake

After the wet cake, containing about 30-35 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS).

Fermenting Organisms

Examples of fermenting organisms used in step c) for fermenting sugars in a fermentation medium into a desired fermentation product include fungal organisms, such as especially yeast. Preferred yeast includes strains of *Saccharomyces* spp., in particular, *Saccharomyces cerevisiae*.

In one embodiment the fermenting organism is added to the fermentation medium, so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED START™ and ETHANOL RED yeast (available from Fermentis/Lesaffre, U.S.A), FALI (available from Fleischmann's Yeast, U.S.A), SUPERSTART and THERMO-SACC™ fresh yeast (available from Ethanol Technology, WI, U.S.A), BIOFERM AFT and XR (available from NABC—North American Bioproducts Corporation, GA, U.S.A), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may be used as fuel which may be blended with gasoline. However, in the case of ethanol it may also be used as potable ethanol.

Recovery

Subsequent to fermentation the fermentation product, such as ethanol, may be separated from the fermentation medium, e.g., by distillation. Alternatively the desired fermentation product may be extracted from the fermentation medium by micro or membrane filtration techniques. The fermentation product may also be recovered by stripping or other method well known in the art.

Use of Protease and Phospholipase for Improving Oil Extraction

In an aspect, the invention relates to the use of a phospholipase, in particular phospholipase C, such as one described above (e.g., any of SEQ ID NOs: 1, 2 and/or 3) for increasing oil recovery yields from thin stillage and/or syrup in a fermentation product production process.

Enzymes

One or more of the following enzyme activities may be used according to the invention.

Alpha-Amylases

The process of the invention, including step (a), may be carried out using a suitable alpha-amylase. In a preferably embodiment a bacterial alpha-amylase and/or a fungal alpha-amylase may be used.

The alpha-amylase may be bacterial when step (a) is carried out as a liquefaction step at high temperatures, i.e., above the initial gelatinization temperature.

The alpha-amylase may be fungal when step (a) is carried out at a temperature below the initial gelatinization temperature, such as when steps (a), (b) and (c) are carried out as a raw starch hydrolysis (single step process or no-cook process) as described above.

Bacterial Alpha-Amylases

Examples of suitable bacterial alpha-amylases include the below mentioned. Preferred bacterial alpha-amylases used in step i) may be derived from a strain the genus *Bacillus* (sometimes referred to as Geo*Bacillus*), including a strain of *Bacillus licheniformis, Bacillus amyloliquefaciens, Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6, 187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or SEQ ID NO: 4 herein, or deletion of amino acids R179+G180 using SEQ ID NO:3 in WO 99/19467 or SEQ ID NO: 4 herein for numbering (which reference is hereby incorporated by reference). Even more preferred are *Bacillus* alpha-amylases, especially *Bacillus stearothermophilus* alpha-amylase, which have a double deletion corresponding to delta(181-182) and optionally further comprising a N193F substitution (also denoted I181*+G182W+N193F) compared to the wild-type BSG alpha-amylase amino acid sequence set forth in SEQ ID NO:3 disclosed in WO 99/19467 or SEQ ID NO: 4 herein.

In an embodiment the *Bacillus stearothermophilus* alpha-amylase is one disclosed in WO 2011/082425, such as one selected from the group of:

I181*+G182*;

I181*+G182*+N193F;

preferably

I181*+G182*+N193F+E129V+K177L+R179E:

I181*+G182*+N193F+V59A+Q89R+E129V+K177L+ R179E+H208Y+K220P+N224L+Q254S;

I181*+G182*+N193F+V59A+Q89R+E129V+K177L+ R179E+Q254S+M284V; and

I181*+G182*+N193F+E129V+K177L+R179E+K220P+ N224L+S242Q+Q254S (using SEQ ID NO: 4 herein for numbering).

In an embodiment the *Bacillus stearothermophilus* alpha-amylase has the following mutations: 181*+G182*+ N193F+V59A+Q89R+E129V+K177L+R179E+Q254S+ M284V (SEQ ID NO: 4).

The truncated *Bacillus stearothermophilus* alpha-amylase is typically naturally truncated to be about 491 amino acids long, such as from 485-495 amino acids long.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+H156Y+ A181T+N190F+I201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TER-MAMYL™ SC, LIQUOZYME™ SC. LIQUOZYME™ LpH, AVANTEC™, AVANTEC™ AMP, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, U.S.A), FUELZYME™ (Verenium, U.S.A).

A bacterial alpha-amylase may be added in step (a) in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of Aspergillus oryzae. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA1 18 and *Athelia rolfsii* SBD and SEQ ID NO: 100 in U.S. 60,638,614), *Rhizomucor pusillus* alpha-amylase with *Athelia rolfsii* AMG linker and SBD (SEQ ID NO:101 in U.S. 60,638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535), and *Meripilus giganteus* alpha-amylase with *Athelia rolfsii* glucoamylase linker and SBD (SEQ ID NO:102 in U.S. 60,638,614). Other specifically contemplated hybrid alpha-amylases are any of the ones listed in Tables 3, 4, 5, and 6 in Example 4 in U.S. application Ser. No. 11/316,535 or WO 2006/069290 (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

In a preferred embodiment the alpha-amylase is one disclosed in WO 2013/006756 including the following variants: *Rhizomucor pusillus* alpha-amylase variant having an *Aspergillus niger* glucoamylase linker and starch-binding domain (SBD) which further comprises at least one of the following substitutions or combinations of substitutions: D165M; Y141W; Y141R; K136F; K192R; P224A; P224R; S123H+Y141W; G2OS+Y141W; A76G+Y141W; G128D+Y141W: G128D+D143N: P219C+Y141W; N142D+D143N; Y141W+K192R; Y141W+D143N; Y141W+N383R; Y141W+P219C+A265C; Y141W+N142D+D143N; Y141W+K192R V410A: G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P2190 (using SEQ ID NO: 2 in WO 2013/006756 for numbering or SEQ ID NO: 5 herein) (all incorporated by reference).

An acid alpha-amylases may according to the invention be added in an amount of 0.1 to 10 AFAU/g DS, preferably 0.10 to 5 AFAU/g DS, especially 0.3 to 2 AFAU/g DS.

Fungal alpha-amylases may be added to step (a) in a well know effective amount, preferably in the range from 0.001-1 mg enzyme protein per g DS, preferably 0.01-0.5 mg enzyme protein per g DS, Carbohydrate-Source Generating Enzyme According to the invention a carbohydrate-source generating enzyme, preferably a glucoamylase, is present in step (b), and may be present and/or added during step (a), saccharification step (b) and/or fermentation step (c) or simultaneous saccharification step (b) and fermentation step (c) (SSF).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used.

Specific examples include glucoamylase (being glucose generators), beta-amylase and maltogenic amylase (being maltose generators).

In a preferred embodiment the carbohydrate-source generating enzyme is a glucoamylase.

Glucoamylases

The process of the invention, including steps (b) and/or (c), may be carried out using any suitable glucoamylase. In a preferably embodiment the glucoamylase is of bacterial or fungal origin.

Contemplated glucoamylases include those from the group consisting of *Aspergillus glucoamylases*, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (AgriC. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al.

(1996), Biochemistry, 35, 8698-8704; and introduction of Pro residues in position A435 and S436 (Li et al. (1997), Protein Eng. 10, 1 199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727.026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Pat. Ser. No. 10/992,187 (hereby incorporated by reference) or sequences having at least 80% or at least 90% identity thereto, In a preferred embodiment the glucoamylase is derived from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*.

In an embodiment the glucoamylase present and/or added during saccharification step (b) and/or fermentation step (c) is of fungal origin, preferably from a strain of *Pycnoporus*, or a strain of *Gloephyllum*. In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ ULTRA, SPIRIZYME™ EXCEL, SPIRIZYME™ ACHIEVE, SPIRIZYME™ B4U and AMG™ E (from Novozymes A/S); OPTIDEX™ 300 (from Genencor Int.): AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS.

Glucoamylase may be added in an effective amount, preferably in the range from 0.001-1 mg enzyme protein per g DS, preferably 0.01-0.5 mg enzyme protein per g dry solid (DS).

Phospholipases

Phospholipases act to hydrolyse phospholipids into their constituent fatty acids and lipophilic moieties. A preferred type of phospholipase is phospholipase C. Suitable phospholipases for use in the invention are derived from organisms, preferably from bacteria or fungi. Preferred phospholipases are derived from *Penicillium emersonii* (e.g., SEQ ID NO: 1 herein), *Bacillus thuringiensis* (e.g., SEQ ID NO: 2 herein) and *Kionochaeata* sp. (e.g., SEQ ID NO: 3 herein), with phospholipase C from *Penicillium emersonii* (SEQ ID NO: 1 herein) being preferred.

The invention is further summarized in the following paragraphs:

1. A process of recovering oil, comprising
   (a) converting a starch-containing material into dextrins with an alpha-amylase;
   (b) saccharifying the dextrins using a carbohydrate source generating enzyme to form a sugar;
   (c) fermenting the sugar in a fermentation medium into a fermentation product using a fermenting organism;
   (d) recovering the fermentation product to form a whole stillage;
   (e) separating the whole stillage into thin stillage and wet cake;
   (e') optionally concentrating the thin stillage into syrup;
   (f) recovering oil from the thin stillage and/or optionally the syrup, wherein a phospholipase is present and/or added during steps (a) to (c).

2. The process of paragraph 1, wherein preferably the phospholipase is present and/or added during steps (b) and/or (c).

3. The process of paragraph 1 or 2, wherein one or more surfactants, preferably non-ionic surfactants, are present and/or added during steps (b) and/or (c).

4. The process of paragraph 3, wherein the non-ionic surfactants are selected from the group of polyethylene glycol sorbitan monooleate (e.g., TWEEN™ 80) and sorbitane monooleate (e.g., SPAN™ 80), or a mixture thereof, such as a 50:50(%) mixture.

5. The process of any of paragraph 1-4 wherein the phospholipase, present and/or added in steps (a) to (c). preferably steps (b) and/or (c), is a phospholipase C.

6. The process of any of paragraph 1-5, wherein the phospholipase, present and/or added in steps (a) to (c), preferably steps (b) and/or (c), has the amino acid sequence of SEQ ID NO: 1 herein (e.g., *Penicillium* PLC); or SEQ ID NO: 2 herein (e.g., *Bacillus*), or SEQ ID NO: 3 herein (e.g., *Kionochaeta* PLC), preferably where the phospholipase has the amino acid sequence of SEQ ID NO: 1 herein.

7. The process of any of paragraph 1-6, wherein the phospholipase. present and/or added in steps (a) to (c), preferably steps (b) and/or (c), is derived from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

8. The process of any of paragraph 1-6, wherein the phospholipase, present and/or added in steps (a) to (c), preferably steps (b) and/or (c), is derived from *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

9. The process of any of paragraph 1-6, wherein the phospholipase, present and/or added in steps (a) to (c), preferably steps (b) and/or (c), is derived from *Kionochaeta*, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

10. The process of recovering oil of any of paragraph 1-9, comprising
    (a) converting a starch-containing material into dextrins with an alpha-amylase at a temperature above the initial gelatinization temperature;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a phospholipase is present and/or added during steps (b) and/or (c).

11. The process of paragraph 10, wherein the temperature in step (a) is above the initial gelatinization temperature, such as at a temperature between 80-90° C., such as around 85° C.

12. The process of paragraph 10 or 11, wherein saccharification step (b) and fermentation step (c) are carried out simultaneously.

13. The process of any of paragraph 10-12, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 4 herein, in particular the *Bacillus stearothermophilus* alpha-amylase is truncated, preferably to have from 485-495 amino acids, such as around 491 amino acids.

14. The process of recovering oil of any of paragraphs 1-9, comprising
    (a) converting a starch-containing material into dextrins with an alpha-amylase at a temperature below the initial gelatinization temperature;
    (b) saccharifying the dextrins using a carbohydrate source generating enzyme to a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a phospholipase is present and/or added during steps (a) to (c).

15. The process of paragraph 14, wherein saccharification step (b) and fermentation step (c) are carried out simultaneously, preferably at a temperature below the initial gelatinization temperature, or sequentially.

16. The process of paragraph 14 or 15, wherein steps (a), (b) and (c) are carried out simultaneously or sequentially at a temperature below the initial gelatinization temperature.

17. Use of a phospholipase for increasing oil recovery yields from thin stillage and/or syrup in a fermentation product production process.

18. The use of paragraph 17, wherein the phospholipase is a phospholipase C.

19. The use of any of paragraph 17-18, wherein the phospholipase has the amino acid sequence of SEQ ID NO: 1 herein; SEQ ID NO: 2 herein; or SEQ ID NO: 3 herein, preferably where the phospholipase has the amino acid sequence of SEQ ID NO: 1 herein.

20. The use of any of paragraph 17-19, wherein the phospholipase is derived from *Penicillium*, such as the phospholipase shown in SEQ ID NO: 1 herein or one having a sequence identity thereto of at least 60%, at least 70%, at least 80%, at least 90%, at least 95%, at least 96%, at least 97%, at least 98%, at least 99%.

21. The use of any of paragraph 17-20, wherein the phospholipase is derived from *Bacillus*, such as the phospholipase shown in SEQ ID NO: 2 herein or one having a sequence identity thereto of at least 60%, at least 70%, at least 80%, at least 90%, at least 95%, at least 96%, at least 97%, at least 98%, at least 99%.

22. The use of any of paragraph 17-21, wherein the phospholipase is derived from *Kionochaeta*, such as the phospholipase shown in SEQ ID NO: 3 herein or one having a sequence identity thereto of at least 60%, at least 70%, at least 80%, at least 90%, at least 95%, at least 96%, at least 97%, at least 98%, at least 99%.

23. The use of any of paragraph 17-22, wherein the phospholipase is combined with one or more surfactants, preferably non-ionic surfactants.

24. The use of paragraph 23, wherein the non-ionic surfactants are selected from the group of polyethylene glycol sorbitan monooleate (e.g., TWEEN™ 80) and sorbitane monooleate (e.g., SPAN™ 80), or a mixture thereof, such as a 50:50(%) mixture.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Alpha-Amylase 369 ("AA369"): *Bacillus stearothermophilus* alpha-amylase with the mutations: I181*+G 182*+N193F+V59A+Q89R+E129V+K177L+R179E+Q254S+M284V truncated to be around 491 amino acids long (SEQ ID NO: 4 herein).

Glucoamylase SA ("GSA") comprises a blend comprising *Talaromyces emersonii* glucoamylase disclosed in WO099/28448, *Trametes cingulata* glucoamylase disclosed as SEQ ID NO: 2 in WO 06/69289, and *Rhizomucor pusillus* alpha-amylase with *Aspergillus niger* glucoamylase linker and SBD disclosed as SEQ ID NO: 5 herein with the following substitutions: G128D+D143N (activity ratio AGU:AGU:FAU(F): approx. 30:7:1).

PLC Pe: *Penicillium emersonii* shown in SEQ ID NO: 1 herein

PLC Bt: *Bacillus thuringiensis* shown in SEQ ID NO: 2 herein

Tween™ 80 is a non-ionic surfactant (polyethylene glycol sorbitan monooleate) purchased from Fisher Scientific as a Fisher Chemical product, CAS: 9005-65-6, Catalog No. T164-500.

SPAN™ 80 is a non-ionic surfactant (Sorbitane monooleate) purchased from Fisher Scientific as a Sigma-Aldrich product, CAS: 1338-43-8, Catalog No, NC0765791.

Determination of Alpha-Amylase Activity

1. Phadebas™ Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in xml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units. In this absorbance range there is linearity between activity and absorbance (Lambert-Beer law). The dilution of the enzyme must therefore be adjusted to fit this criterion. Under a specified set of conditions (temperature, pH, reaction time, buffer conditions) 1 mg of a given alpha-amylase will hydrolyze a certain amount of substrate and a blue colour will be produced. The measured absorbance is directly proportional to the specific activity (activity/mg of pure alpha-amylase protein) of the alpha-amylase in question under the given set of conditions.

2. Alternative Method

Alpha-amylase activity is alternatively determined by a method employing the PNP-G7 substrate, PNP-G7 which is an abbreviation for p-nitrophenyl-alpha,D-maltoheptaoside, which is a blocked oligosaccharide that can be cleaved by an endo-amylase. Following the cleavage, the alpha-glucosidase included in the kit digest the substrate to liberate a free PNP molecule which has a yellow colour and thus can be measured by visible spectophometry at wavelength Lambda=405 nm (400-420 nm). Kits containing PNP-G7 substrate and alpha-glucosidase are manufactured by Bohringer-Mannheim (cat. No. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-glucosidase solution with 0.5 ml substrate, The assay is performed by transforming 20 microL enzyme solution to a 96 well microtitre plate and incubating at 25° C., 200 microL working solution, 25° C. is added. The solution is mixed and pre-incubated 1 minute and absorption is measured every 15 seconds over 3 minutes at OD 405 nm.

The slope of the time dependent absorption-curve is directly proportional to the specific activity (activity per mg enzyme) of the alpha-amylase in question under the given set of conditions.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
|---|---|
| Temperature | 37° C. |
| pH | 4.7 |
| Reaction time | 7-20 minutes |

A detailed description of Novozymes' method for determining KNU and FAU is available on request as standard method EB-SM-0009.02/01. Determination of acid alpha-amylase activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S).

The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

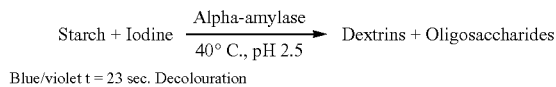

$$\text{Starch} + \text{Iodine} \xrightarrow[40^\circ \text{C., pH 2.5}]{\text{Alpha-amylase}} \text{Dextrins} + \text{Oligosaccharides}$$

Blue/violet t = 23 sec. Decolouration

Standard conditions/reaction conditions: (per minute)

Substrate: starch, approx. 0.17 g/L

Buffer: Citrate, approx. 0.03 M

Iodine ($I_2$): 0.03 g/L $CaCl_2$: 1.85 mM pH: 2.50±0.05

Incubation temperature: 40° C.

Reaction time: 23 seconds

Wavelength: Lambda=590 nm

Enzyme concentration: 0.025 AFAU/mL

Enzyme working range: 0.01-0.04 AFAU/mL

Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum soluble.

A folder EB-SM-0009.02/01 describing this analytical method in more detail is available upon request to Novozymes A S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:

| | |
|---|---|
| Substrate: | maltose 23.2 mM |
| Buffer: acetate | 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH; | 430 U/L |
| Mutarotase: | 9 U/L |
| NAD: | 0.21 mM |
| Buffer: | phosphate 0.12 M; 015 M NaCl |
| pH: | 7.60 ± 0.05 |
| Incubation temperature: | 37° C. ± 1 |
| Reaction time: | 5 minutes |
| Wavelength; | 340 nm |

A folder (EB-SM-0131.02/01) describing this analytical method in more detail is available on request from Novozymes A/S, Denmark, which folder is hereby included by reference.

Determination of Protease Activity (AU)

Dimethyl casein (DMC) is hydrolyzed by the proteolytic enzyme to small peptides. The primary amino groups formed in this process react with trinitrobenzene sulphonic acid (TNBS) forming a coloured complex. This colour development is monitored in situ so the change in absorption per time unit can be calculated. This figure is a measure of the reaction rate and thus of the enzyme activity.

| Reaction conditions for the DMC reaction | |
|---|---|
| Temperature: | 50° C. |
| pH: | 8.3 |
| Wavelength: | 405 nm |
| Reaction time: | 8 min. |
| Measuring time: | 2 min. |
| Enzyme concentration range: | 0.072-0.216 mAU/ml. |

The activity is determined relative to an enzyme standard.

The assay is further described in standard method document EB-SM-0218.02/02 available upon request from Novozymes A/S, Denmark.

EXAMPLES

Example 1

Extracting Free Oil Using Phospholipase and Surfactant

The purpose of this experiment is to measure the free corn oil yield increase realized through the use of one of two PLC enzymes, either *Penicillium emersonii* PLC (PLC Pe) or *Bacillus thuringiensis* PLC (PLC Bt), and a dose response of a surfactant blend consisting of 50% TWEEN® 80 and 50% SPAN® 80 with or without PLC.

Method

Fermentation: Industrially mash liquefied with Alpha-Amylase 369 was stored frozen. One liter of mash was thawed for approximately 2 hours prior to starting this study. The dry solids content of the mash was measured on a Mettler-Toledo moisture balance, with a resulting value of 33.70% DS. The mash was prepared to 1000 ppm urea and 3 mg/L penicillin using solutions of 200 g/L urea and 1 g/L penicillin, respectively, and adjusted to pH 5 using 40% v/v $H_2SO_4$. Approximately 27 g of each prepared mash was pipetted into each of 45 pre-weighed 50 mL centrifuge tubes, which had holes drilled in the top.

The PLCs used were *Penicillium emersonii* (PLC Pe) and *Bacillus thuringiensis* PLC (PLC Bt). The surfactant used was a blend consisting of 50% w/w TWEEN™ 80 and 50% w/w SPAN™ 80, based on surfactant optimization reported by Wang, et al (Fang, L., Wang, T., & Lamsal, B. (2015). Synergistic effect of surfactants and silica nanoparticles on oil recovery from condensed corn distillers solubles (CODS). Industrial Crops & Products. 553. doi:10.1016/j.indcrop.2015.09.031).

RED STAR™ yeast (*Saccharomyces cerevisiae*) was rehydrated, with 2.75 g of yeast placed in 50 of 32° C. tap water for 30 minutes.

TABLE

Treatments tested

| Treatment | Glucoamylase | Glucoamylase Dose (AGU/gDS) | PLC | PLC Dose (μg/gDS) | Surfactant Dose (% w/w) |
|---|---|---|---|---|---|
| 1 | GSA | 0.6 | Control | 0 | 0.00% |
| 2 | GSA | 0.6 | Control | 0 | 0.03% |
| 3 | GSA | 0.6 | Control | 0 | 0.05% |
| 4 | GSA | 0.6 | Control | 0 | 0.08% |
| 5 | GSA | 0.6 | Control | 0 | 0.10% |
| 6 | GSA | 0.6 | P. emersonii | 20 | 0.00% |
| 7 | GSA | 0.6 | P. emersonii | 20 | 0.03% |
| 8 | GSA | 0.6 | P. emersonii | 20 | 0.05% |
| 9 | GSA | 0.6 | P. emersonii | 20 | 0.08% |
| 10 | GSA | 0.6 | P. emersonii | 20 | 0.10% |
| 11 | GSA | 0.6 | B. thuringiensis | 20 | 0.00% |
| 12 | GSA | 0.6 | B. thuringiensis | 20 | 0.03% |
| 13 | GSA | 0.6 | B. thuringiensis | 20 | 0.05% |
| 14 | GSA | 0.6 | B. thuringiensis | 20 | 0.08% |
| 15 | GSA | 0.6 | B. thuringiensis | 20 | 0.10% |

TABLE

Enzymes

| Name | stock conc. | Units | Dilution (X) | expt. conc | units |
|---|---|---|---|---|---|
| P. emersonii | 24 | mg/mL | 6.5 | 3.67 | μg/μL |
| B. thuringiensis | 11 | mg/g | 3.1 | 3.54 | μg/μL |
| Glycoamylase SA (GSA) | 1234 | AGU/g | 10.0 | 0.12 | AGU/μL |

Enzyme doses were calculated via the following equation, or similar:

$$Enz.dose(\text{ml}) = \frac{\text{Final enz. dose } (AGU/g\ DS) \times \text{Mash weight } (g) \times \text{Solid content } (\%DS)}{\text{Conc. enzyme } (mg\ AGU/ml)}$$

TABLE

Enzyme Dosing

| Tube # | PLC | PLC Dose (μl) | GSA Dose (μl) | Yeast (μl) | H2O |
|---|---|---|---|---|---|
| 1 | Control | 0.0 | 44.1 | 250 | 75.3 |
| 2 | Control | 0.0 | 43.9 | 250 | 72.6 |
| 3 | Control | 0.0 | 43.8 | 250 | 71.0 |
| 4 | Control | 0.0 | 43.7 | 250 | 69.6 |
| 5 | Control | 0.0 | 43.7 | 250 | 69.8 |
| 6 | Control | 0.0 | 43.5 | 250 | 67.5 |
| 7 | Control | 0.0 | 43.9 | 250 | 72.6 |
| 8 | Control | 0.0 | 44.0 | 250 | 73.7 |
| 9 | Control | 0.0 | 44.0 | 250 | 74.4 |
| 10 | Control | 0.0 | 44.0 | 250 | 74.2 |
| 11 | Control | 0.0 | 43.7 | 250 | 70.7 |
| 12 | Control | 0.0 | 43.7 | 250 | 70.6 |
| 13 | Control | 0.0 | 43.6 | 250 | 69.0 |
| 14 | Control | 0.0 | 44.1 | 250 | 74.7 |
| 15 | Control | 0.0 | 43.9 | 250 | 73.1 |
| 16 | P. emersonii | 48.9 | 43.7 | 250 | 20.7 |
| 17 | P. emersonii | 49.5 | 44.2 | 250 | 27.0 |
| 18 | P. emersonii | 49.3 | 44.0 | 250 | 24.4 |
| 19 | P. emersonii | 49.1 | 43.8 | 250 | 22.4 |
| 20 | P. emersonii | 48.9 | 43.6 | 250 | 20.5 |
| 21 | P. emersonii | 49.1 | 43.8 | 250 | 22.5 |
| 22 | P. emersonii | 49.0 | 43.7 | 250 | 21.3 |
| 23 | P. emersonii | 48.9 | 43.6 | 250 | 20.5 |
| 24 | P. emersonii | 49.2 | 43.9 | 250 | 24.0 |
| 25 | P. emersonii | 49.4 | 44.1 | 250 | 26.1 |
| 26 | P. emersonii | 49.1 | 43.8 | 250 | 21.9 |
| 27 | P. emersonii | 48.6 | 43.4 | 250 | 17.0 |
| 28 | P. emersonii | 49.0 | 43.8 | 250 | 21.9 |
| 29 | P. emersonii | 49.3 | 44.0 | 250 | 24.6 |
| 30 | P. emersonii | 49.3 | 44.0 | 250 | 24.2 |
| 31 | B. thuringiensis | 50.8 | 43.8 | 250 | 20.0 |
| 32 | B. thuringiensis | 50.8 | 43.7 | 250 | 19.7 |
| 33 | B. thuringiensis | 51.0 | 43.9 | 250 | 21.5 |
| 34 | B. thuringiensis | 51.1 | 44.0 | 250 | 23.0 |
| 35 | B. thuringiensis | 50.8 | 43.8 | 250 | 20.2 |
| 36 | B. thuringiensis | 50.9 | 43.8 | 250 | 20.8 |
| 37 | B. thuringiensis | 51.3 | 44.1 | 250 | 24,7 |
| 38 | B. thuringiensis | 51.4 | 44.2 | 250 | 25.9 |
| 39 | B. thuringiensis | 51.0 | 43.9 | 250 | 21.5 |
| 40 | B. thuringiensis | 50.9 | 43.8 | 250 | 20.5 |
| 41 | B. thuringiensis | 52.0 | 44.8 | 250 | 32.4 |
| 42 | B. thuringiensis | 50.9 | 43.8 | 250 | 21.1 |
| 43 | B. thuringiensis | 50.4 | 43.4 | 250 | 15.7 |
| 44 | B. thuringiensis | 51.2 | 44.1 | 250 | 23.6 |
| 45 | B. thuringiensis | 50.9 | 43.8 | 250 | 20.7 |

Water was dosed into each sample such that the total added volume of enzyme and water was 621 μL/27 g sample. All samples were dosed with 250 μL of rehydrated yeast solution and vortexed. Each sample was weighed when all samples had been dosed. The samples were placed in a shaking incubator set at 32° C. for 64 hours.

Free Oil Assay: The sample tubes are then processed on an assay validated to measure the free extractable oil. This assay consists of dosing the tubes with surfactant, incubating at 65° C. for 10 minutes, and centrifuging at 3000×g for 10 minutes. The tubes are then carefully rinsed with hexane multiple times in order to extract hexane from the top surface (free) oil layer. The hexane wash consists of five rinses: 10 mL, 5 mL, 5 mL, 2.5 mL, 2.5 mL. The collected hexane/oil mixture for each tube is then evaporated on a Buchi Multivapor to isolate the corn oil. The weight of the corn oil is then taken and normalized to the starting material.

Figure 2:
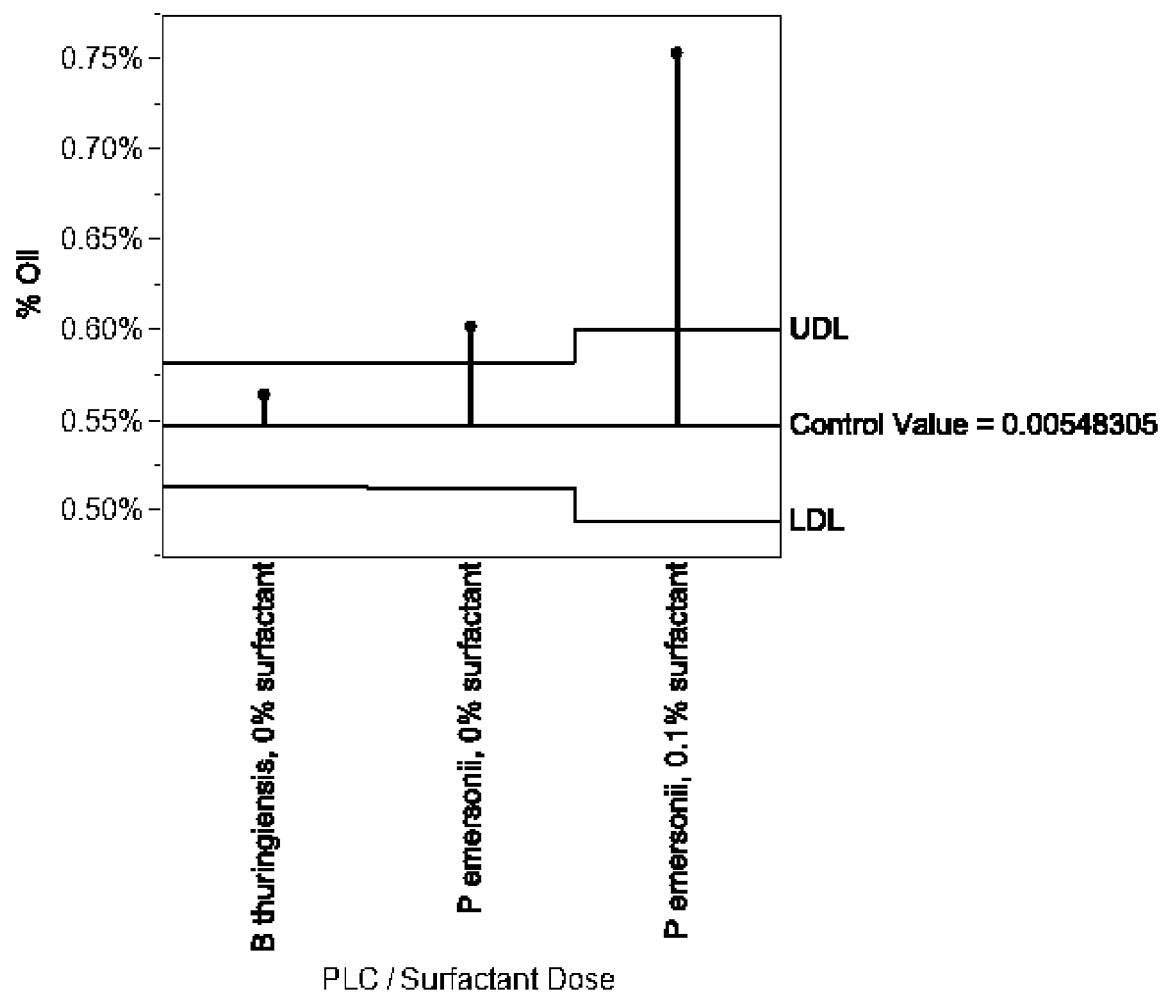
FIG. 2 shows the % oil vs PLC/Surfactant dose.
Figure 3:
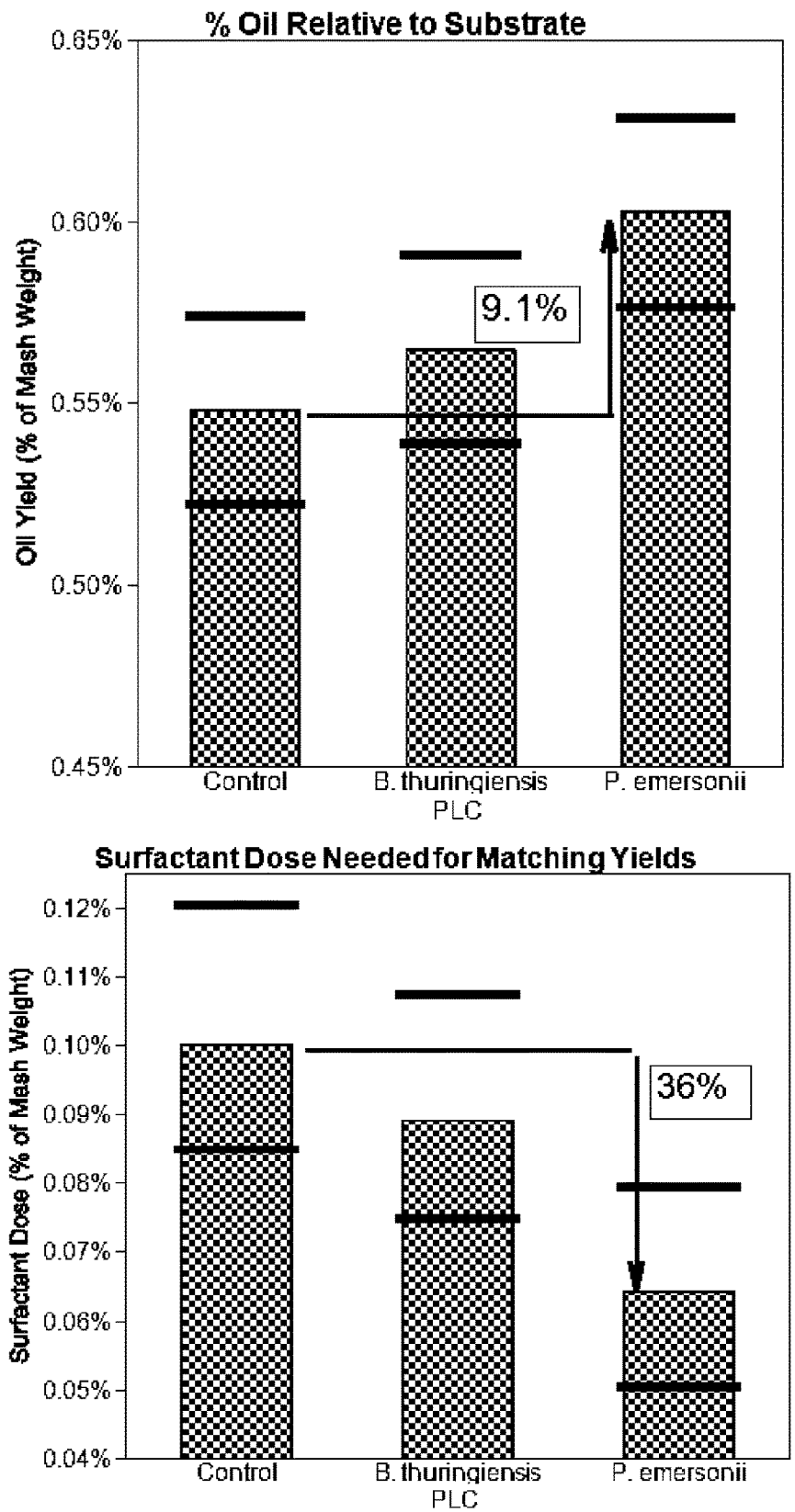
FIG. 3 shows the oil yield for PLC Pe, PLC Bt and a Control and surfactant dose needed for matching yields.

The results are shown in FIGS. 1-3. Statistical analysis, performed in JMP 12.0.1 using the Fit Model platform, revealed that the addition of surfactant linearly increased oil yields for the control and both PLC treatments. In this model, the *P. emersonii* PLC also significantly improved oil yields over the control, increasing free oil by 9.1%.

One thing to note is that the slope of oil yield relative to surfactant is the same for both PLCs and for the control.

The increase in oil yield due to the addition of *P. emersonii* PLC was found to be significant relative to the control, as previously mentioned (FIG. 2).

Without using any surfactant, the free oil yield is increased by 9.1% relative to the control by application of the *P. emersonii* PLC (see FIG. 3), Alternatively, by adding the *P. emersonii* PLC, the required surfactant dose to maintain the top measured yield with no PLC can be reduced by 36% (FIG. 3).

Conclusion

The use of PLC can increase free oil yields by 9.1%, or reduce the necessary surfactant dose by 36%.

The invention claimed is:

1. A process of recovering oil, comprising:
   (a) converting starch-containing material into dextrins with an alpha amylase, wherein the starch-containing material comprises corn;
   (b) saccharifying the dextrins with a glucoamylase to form a sugar;
   (c) fermenting the sugar in a fermentation medium with yeast into a fermentation product, wherein the fermentation product comprises ethanol;
   (d) recovering the fermentation product to form a whole stillage;
   (e) separating the whole stillage into thin stillage and wet cake;
   (f) concentrating the thin stillage into syrup;
   (g) recovering oil from the thin stillage and/or the syrup, wherein a phospholipase C is present and/or added during steps (a) to (c), and wherein oil yield is increased compared to a control process without phospholipase C.

2. The process of claim 1, wherein the phospholipase C is present during steps (b) or (c).

3. The process of claim 1, wherein the phospholipase C is present during steps (b) and (c).

4. The process of claim 1, wherein the phospholipase C is added during steps (b) or (c).

5. The process of claim 1, wherein the phospholipase C is added during steps (b) and (c).

6. The process of claim 1, wherein one or more surfactants are present and/or added during steps (b) and/or (c).

7. The process of claim 6, wherein the surfactants comprise non-ionic surfactants and are selected from the group consisting of: polyethylene glycol sorbitan monooleate, sorbitane monooleate, and a mixture thereof.

8. The process of claim 1, comprising:
   (a) converting the starch-containing material into dextrins with the alpha-amylase at a temperature above the initial gelatinization temperature;
   (b) saccharifying the dextrins using the glucoamylase to form the sugar;
   (c) fermenting the sugar in a fermentation medium into the fermentation product with the yeast;
   (d) recovering the fermentation product to form the whole stillage;
   (e) separating the whole stillage into thin stillage and wet cake;
   (f) concentrating the thin stillage into syrup;
   (g) recovering oil from the thin stillage and/or the syrup, wherein the phospholipase C is present and/or added during steps (b) and/or (c).

9. The process of claim 8, wherein step (b) and step (c) are carried out sequentially.

10. The process of claim 8, wherein step (b) and step (c) are carried out simultaneously.

11. The process of claim 10, wherein the phospholipase C is present during steps (b) and (c).

12. The process of claim 10, wherein the phospholipase C is added during steps (b) and (c).

13. The process of claim 1, comprising:
   (a) converting the starch-containing material into dextrins with the alpha-amylase at a temperature below the initial gelatinization temperature;
   (b) saccharifying the dextrins with the glucoamylase to form the sugar;
   (c) fermenting the sugar in the fermentation medium into the fermentation product with the yeast;
   (d) recovering the fermentation product to form the whole stillage;
   (e) separating the whole stillage into thin stillage and wet cake;

(f) concentrating the thin stillage into syrup;
(g) recovering oil from the thin stillage and/or the syrup, wherein the phospholipase C is present and/or added during steps (a) to (c).

14. The process of claim 13, wherein step (b) and step (c) are carried out sequentially.

15. The process of claim 13, wherein step (b) and step (c) are carried out simultaneously.

16. The process of claim 13, wherein steps (a), (b) and (c) are carried out sequentially at the temperature below the initial gelatinization temperature.

17. The process of claim 13, wherein steps (a), (b) and (c) are carried out simultaneously at the temperature below the initial gelatinization temperature.

18. The process of claim 17, wherein the phospholipase C is present during steps (a), (b) and (c).

19. The process of claim 17, wherein the phospholipase C is added during steps (a), (b) and (c).

\* \* \* \* \*